(12) United States Patent
Proksa

(10) Patent No.: US 7,894,569 B2
(45) Date of Patent: Feb. 22, 2011

(54) MEDICAL X-RAY EXAMINATION APPARATUS FOR PERFORMING K-EDGE IMAGING

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/743,867

(22) PCT Filed: Nov. 14, 2008

(86) PCT No.: PCT/IB2008/054775

§ 371 (c)(1),
(2), (4) Date: May 20, 2010

(87) PCT Pub. No.: WO2009/066214

PCT Pub. Date: May 28, 2009

(65) Prior Publication Data

US 2010/0310035 A1    Dec. 9, 2010

(30) Foreign Application Priority Data

Nov. 23, 2007   (EP)   ................... 07121406

(51) Int. Cl.
*A61B 6/00* (2006.01)
(52) U.S. Cl. .......................... 378/5; 382/128
(58) Field of Classification Search ............... 378/4, 378/5
See application file for complete search history.

(56) References Cited

U.S. PATENT DOCUMENTS

| | | | |
|---|---|---|---|
| 4,686,695 A * | 8/1987 | Macovski | 378/146 |
| 6,512,807 B1 | 1/2003 | Pohlman et al. | |
| 6,990,222 B2 * | 1/2006 | Arnold | 382/131 |
| 7,006,677 B2 | 2/2006 | Manjeshwar et al. | |

(Continued)

FOREIGN PATENT DOCUMENTS

WO    2007034356 A2    3/2007

OTHER PUBLICATIONS

Gillam et al., K-edge subtraction using an energy-resolving position-sensitive detector, Nuclear Instruments and Methods in Physics Research A 604, 2009, pp. 97-100.*

(Continued)

*Primary Examiner*—Edward J Glick
*Assistant Examiner*—Alexander H Taningco

(57) ABSTRACT

The invention relates to a medical X-ray examination apparatus (1) for performing K-edge imaging. The medical X-ray examination apparatus (1) comprises an imaging unit (21), which is configured to spectrally decompose an X-ray absorption spectrum to image the X-ray absorption spectrum as a conventional X-ray absorption image (23*a*) and a K-edge absorption image (23*b*). The conventional X-ray absorption image (23*a*) includes data elements representing the anatomical background of an object of interest. The K-edge absorption image (23*b*) includes data elements representing quantitative information of local densities of material showing K-edge absorption within the object of interest. The imaging unit (21) comprises a spatial resolution reducer for reducing the spatial resolution of the K-edge absorption image, so that with a medical X-ray examination apparatus according to the invention an increased sensitivity of the selective imaging of a K-edge absorption image is achieved as compared to the sensitivity of the selective imaging of a K-edge absorption image of a known medical X-ray examination apparatus.

6 Claims, 1 Drawing Sheet

U.S. PATENT DOCUMENTS

| | | | |
|---|---|---|---|
| 7,103,224 | B2 | 9/2006 | Ashton |
| 7,539,337 | B2* | 5/2009 | Simanovsky et al. ........ 382/131 |
| 7,583,779 | B2* | 9/2009 | Tkaczyk et al. ................ 378/4 |
| 2007/0047786 | A1 | 3/2007 | Aklilu et al. |
| 2008/0253503 | A1* | 10/2008 | Proksa ........................... 378/5 |

OTHER PUBLICATIONS

Abudurexiti et al., Demonstration of iodine K-edge imaging by use of an energy-discrimination X-ray computed tomography system with a cadmium telluride detector, Radiol Phys Technol, 2010, pp. 127-135.*

Schlomka et al., Experimental feasibility of multi-energy photon-counting K-edge imagin in pre-clinical computed tomography, Phys Med Biol, 53, 2008, pp. 4031-4047.*

Roessl et al: "K-edge imaging in x-ray computed tomography using multi-bin photon counting detectors"; Physics in Medicine and Biology, vol. 52, No. 15, (2007), pp. 4679-4696.

Sarnelli et al: "K-edge digital subtraction imaging with dicromatic x-ray sources: SNR and Dose Studies"; Physics in Medicine and Biology, vol. 51, No. 17 (2006), pp. 4311-4328.

* cited by examiner ly low. When using the known medical X-ray examination apparatus, a large number of potential clinical applications either suffer from this limited sensitivity or are completely impossible because of the low sensitivity.
MEDICAL X-RAY EXAMINATION APPARATUS FOR PERFORMING K-EDGE IMAGING

FIELD OF THE INVENTION

The invention relates to a medical X-ray examination apparatus for performing K-edge imaging, comprising an imaging unit which is configured to spectrally decompose an X-ray absorption spectrum to image the X-ray absorption spectrum as:
- a conventional X-ray absorption image, including data elements representing the anatomical background of an object of interest, and
- a K-edge absorption image, including data elements representing quantitative information of local densities of material showing K-edge absorption within the object of interest.

BACKGROUND OF THE INVENTION

Such a medical X-ray examination apparatus is known from the scientific article "K-edge imaging in X-ray computed tomography using multi-bin photon counting detectors" (Phys. Med. Biol. 52, (2007) 4679-4696). The known medical X-ray examination apparatus is a computed tomography (CT) scanner comprising an imaging unit with a multi-bin X-ray photon counting detector. This imaging unit allows to spectrally decompose an X-ray absorption spectrum to image the X-ray absorption spectrum as a conventional X-ray absorption image and a K-edge absorption image.

The conventional X-ray absorption image is equal to the image of a conventional X-ray absorption spectrum which is acquired with an imaging unit comprising a conventional current integrating X-ray detector. The conventional X-ray absorption image includes data elements representing the anatomical background of an object of interest. The K-edge absorption image is an X-ray absorption image of material within the object of interest, said material having its K-edge absorption within the energy range of the known medical X-ray examination apparatus. The K-edge absorption image includes data elements representing quantitative information of local densities of material showing K-edge absorption within the object of interest.

The known medical X-ray examination apparatus allows selective imaging of material having its K-edge absorption in the energy range of the known medical X-ray examination apparatus, (e.g. gadolinium-based targeted contrast agents), in addition to conventional imaging of the anatomical background.

A disadvantage of the known medical X-ray examination apparatus is that the sensitivity of the selective imaging of a K-edge absorption image is relatively low. When using the known medical X-ray examination apparatus, a large number of potential clinical applications either suffer from this limited sensitivity or are completely impossible because of the low sensitivity.

SUMMARY OF THE INVENTION

It is an object of the invention to provide a medical X-ray examination apparatus of the kind mentioned in the opening paragraph with an increased sensitivity of the selective imaging of a K-edge absorption image, so that the medical X-ray examination apparatus according to the invention can be used for more clinical applications than the known medical X-ray examination apparatus.

This object is achieved by a medical X-ray examination apparatus according to the invention, characterized in that the imaging unit comprises a spatial resolution reducer for reducing the spatial resolution of the K-edge absorption image.

By using a spatial reducer to reduce the spatial resolution of the K-edge absorption image, a plurality of interconnected data elements containing image information of the K-edge absorption image is combined. By combining these data elements, the signal to noise ratio (SNR) of the K-edge absorption image is improved. Since the sensitivity of the selective imaging of a K-edge absorption image is at least partially determined by the SNR of the K-edge absorption image, an improved SNR directly contributes to a better sensitivity of the selective imaging of a K-edge absorption image. With an increased sensitivity of the selective imaging of a K-edge absorption image, the medical X-ray examination apparatus according to the invention can be used for more clinical applications than the known medical X-ray examination apparatus.

A further advantage of the medical X-ray examination apparatus according to the invention is that when the SNR of the K-edge absorption image is improved, the quantitative information of the local densities of the K-edge material that has bound to an object of interest becomes more accurate (i.e. when the SNR of the K-edge absorption image is improved, the quantitative information of the local densities of targeted contrast agents having a payload of K-edge material, like gadolinium-based targeted contrast agents, that has bound to an object of interest (e.g. a tumor, soft plaque in coronaries, a lesion etc.) becomes more accurate). This corresponds well to the clinical evolution towards clinical requests for quantitative measures that inform physicians about how much K-edge material has bound to an object of interest.

A preferred embodiment of the medical X-ray examination apparatus according to the invention is characterized in that the spatial resolution reducer comprises a cluster-defining unit for defining clusters of a plurality of individual data elements which are interconnected in the K-edge absorption image, and comprises a replacement unit for replacing the quantitative information represented by the individual data elements with the quantitative information represented by the clusters of data elements. To ensure an improvement of the SNR of a K-edge absorption image and thus of the sensitivity of the selective imaging of a K-edge absorption image, the cluster-defining unit defines clusters wherein all individual data elements contain image information, i.e. wherein all individual data elements represent quantitative information of the local densities of the K-edge material. The replacement unit, which replaces the quantitative information represented by the individual data elements with the quantitative information represented by the clusters of data elements, provides a single quantitative measure per cluster of how much K-edge material has bound to an object of interest. Together with this quantitative measure per cluster, for each cluster the position of the cluster within the anatomical background and its shape are shown in the conventional X-ray absorption image.

A further preferred embodiment of the medical X-ray examination apparatus according to the invention is characterized in that the replacement unit comprises a filter for replacing the quantitative information represented by the individual data elements with the quantitative information represented by the clusters of data elements. An advantage of this embodiment is that a filter is a relatively simple solution to replace the quantitative information represented by the individual data elements with quantitative information represented by the clusters of data elements. The quantitative information represented by the clusters of individual data elements can be the sum or the average of the quantitative information represented by the individual data elements of the clusters, although other filter algorithms are also possible.

A further preferred embodiment of the medical X-ray examination apparatus according to the invention is characterized in that the spatial resolution reducer comprises a replacement combiner unit for combining the quantitative information represented by the clusters of individual data elements into a single quantitative measure. The replacement combiner unit combines the quantitative information represented by all clusters within an object of interest into a single quantitative measure, which reduces the clinical output. Because of the reduced clinical output, i.e. the single quantitative measure together with information of the position of the clusters within the anatomical background and the shape of the clusters which are shown in the conventional X-ray absorption image, physicians will be able to come to their diagnostic decisions in a more efficient way than with the known medical X-ray examination apparatus.

An even further preferred embodiment of the medical X-ray examination apparatus according to the invention is characterized in that the cluster-defining unit is configured to define clusters of a plurality of individual data elements which are interconnected in the K-edge absorption image, based on model constraints. To optimize the process of defining clusters so that the clusters represent a (part of a) real anatomical object (e.g. a tumor, soft plaque in coronaries, a lesion etc.), the cluster-defining unit is configured to define clusters based on model constraints, wherein a large number of different models or heuristics can be used to provide good clustering results.

A further embodiment of the medical X-ray examination apparatus according to the invention is characterized in that the medical X-ray examination apparatus is a CT scanner.

BRIEF DESCRIPTION OF THE DRAWINGS

These and other aspects of the invention will be elucidated with reference to the drawing, wherein.

DETAILED DESCRIPTION OF THE INVENTION

Figure 1:
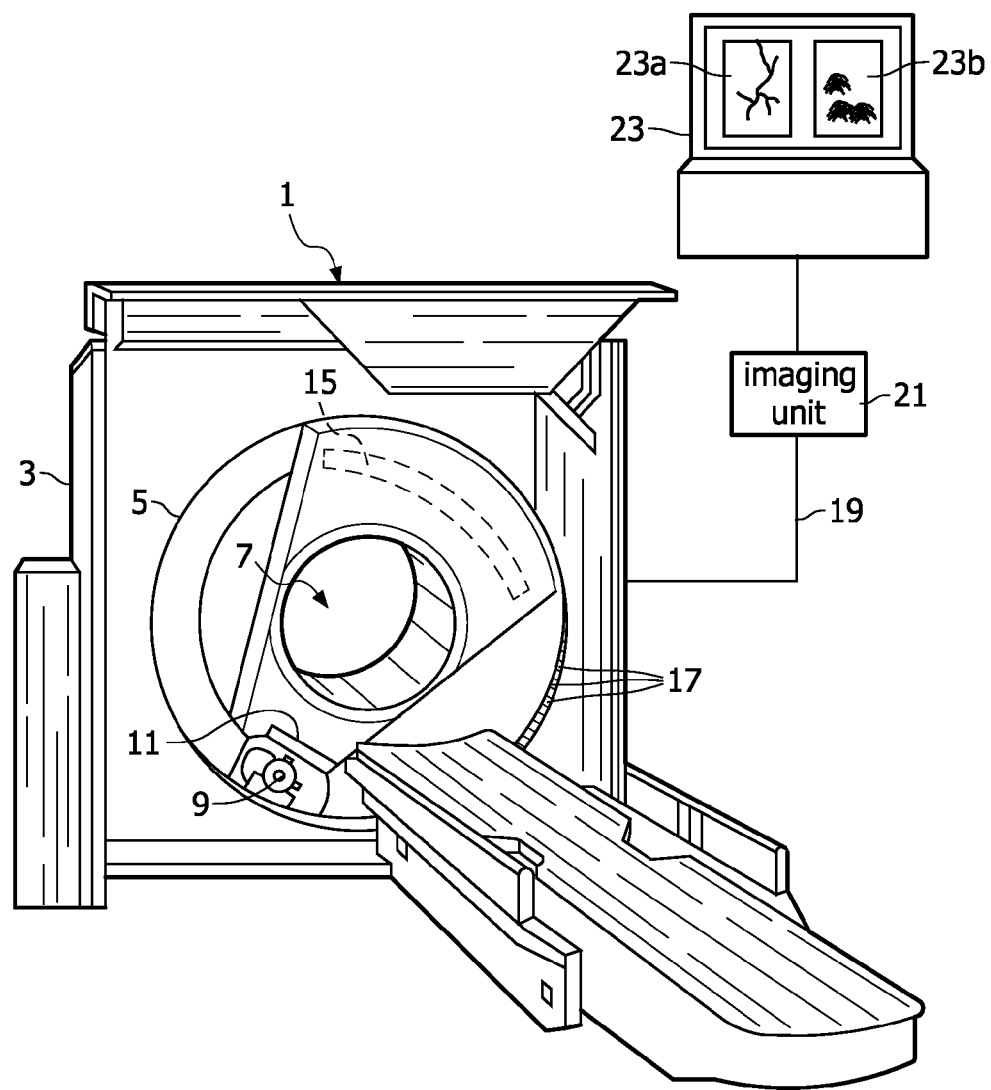
FIG. 1 is a diagrammatic illustration of a CT scanner according to the invention.

FIG. 1 is diagrammatic illustration of a CT scanner 1 according to the invention. The CT scanner 1 includes a stationary gantry 3 and a rotating gantry 5 which define an examination region 7. The rotating gantry 5 is suspended from the stationary gantry 3 for rotation about the examination region 7. A radiation source 9, such as an X-ray tube, is arranged on the rotating gantry 5 for rotation therewith. The radiation source 9 produces a beam of penetrating radiation that passes through the examination region 7 as the rotating gantry 5 is rotated by an external motor (not shown) about a longitudinal axis of the examination region 7. A collimator and shutter assembly 11 forms the beam of penetrating radiation into a cone shape and selectively gates the beam on and off. Alternately, the radiation beam is gated on and off electronically at the source 9. A patient support table 13 supports an object or a patient to be examined. The patient support table 13 is positioned such that the object or the patient to be examined is located at least partially within the examination region 7. The cone-shaped beam of radiation defines a volume through the object or patient to be examined, which is repeatedly imaged over a period of time.

When performing K-edge imaging with the CT scanner according to the invention, usually a targeted contrast agent having a payload of K-edge material is supplied to the object or the patient to be examined. An example of such a targeted contrast agent is a gadolinium-based targeted contrast agent, although other targeted contrast agents based on gold, bismuth or similar elements are also possible. The payload of K-edge material binds to an object of interest (e.g. a tumor, soft plaque in coronaries, a lesion etc.). The CT scanner according to the invention comprises either an array of radiation detectors 15 which are mounted peripherally across from the source on the rotating gantry 5, or a stationary ring of radiation detectors 17 which is mounted around the stationary gantry 3. Either the array of radiation detectors 15 or the stationary ring of radiation detectors 17 measures an X-ray absorption spectrum resulting from the penetrating radiation emitted by the radiation source 9 and the absorption of this radiation by an object or patient to be examined which is at least partially located in the examination region 7. Via a data line 19 the measured X-ray absorption spectrum is supplied to an imaging unit 21. The imaging unit 21 spectrally decomposes the measured X-ray absorption spectrum so that it is imaged on a display 23 as a conventional X-ray absorption image 23a, including data elements representing the anatomical background of the object of interest, and a K-edge absorption image 23b, including data elements representing quantitative information of local densities of material showing K-edge absorption within the object of interest. The imaging unit comprises a spatial resolution reducer (not shown) which reduces the spatial resolution of the K-edge absorption image so that with a CT scanner according to the invention an increased sensitivity of the selective imaging of a K-edge absorption image is achieved as compared to the sensitivity of the selective imaging of a K-edge absorption image of a known medical X-ray examination apparatus.

The invention claimed is:

1. A medical X-ray examination apparatus (1) for performing K-edge imaging, comprising an imaging unit (21) which is configured to spectrally decompose an X-ray absorption spectrum to image the X-ray absorption spectrum as:

a conventional X-ray absorption image (23a), including data elements representing the anatomical background of an object of interest, and a K-edge absorption image (23b), including data elements representing quantitative information of local densities of material showing K-edge absorption within the object of interest, characterized in that the imaging unit comprises a spatial resolution reducer for reducing the spatial resolution of the K-edge absorption image.

2. A medical X-ray examination apparatus (1) as claimed in claim 1, characterized in that the spatial resolution reducer comprises a cluster-defining unit for defining clusters of a plurality of individual data elements which are interconnected in the K-edge absorption image (23b), and comprises a replacement unit for replacing the quantitative information represented by the individual data elements with the quantitative information represented by the clusters of data elements.

3. A medical X-ray examination apparatus (1) as claimed in claim 2, characterized in that the replacement unit comprises a filter for replacing the quantitative information represented by the individual data elements with the quantitative information represented by the clusters of data elements.

4. A medical X-ray examination apparatus (1) as claimed in claim 2,
characterized in that the spatial resolution reducer comprises a replacement combiner unit for combining the quantitative information represented by the clusters of individual data elements into a single quantitative measure.

5. A medical X-ray examination apparatus (1) as claimed in claim 2, characterized in that the cluster-defining unit (21) is configured to define clusters of a plurality of individual data elements which are interconnected in the K-edge absorption image (23*b*), based on model constraints.

6. A medical X-ray examination apparatus (1) as claimed in claim 1, characterized in that the medical X-ray examination apparatus is a CT scanner.

\* \* \* \* \*